United States Patent [19]

Deutsch

[11] Patent Number: 4,762,798

[45] Date of Patent: Aug. 9, 1988

[54] DEVICE AND METHOD FOR DETERMINING A CHARACTERISTIC OF A FLUID SAMPLE

[75] Inventor: Marshall E. Deutsch, Sudbury, Mass.

[73] Assignee: Marshall Diagnostics, Inc., Bedford, Mass.

[21] Appl. No.: 815,233

[22] Filed: Dec. 31, 1985

[51] Int. Cl.⁴ .................. G01N 21/78; G01N 33/72
[52] U.S. Cl. ............................ 436/67; 356/246; 356/413; 422/58; 422/61; 422/102; 436/165
[58] Field of Search ............. 422/58, 102, 61; 436/165, 166, 67; 356/413, 246

[56] References Cited

U.S. PATENT DOCUMENTS

| | | | |
|---|---|---|---|
| 2,912,895 | 11/1959 | Hamilton | 356/413 |
| 3,027,799 | 4/1962 | Weichselbaum | 356/246 |
| 4,027,660 | 6/1977 | Wardlaw et al. | 356/246 X |
| 4,105,415 | 8/1978 | Lovett | 356/246 X |
| 4,427,634 | 1/1984 | Truglio | 356/246 X |
| 4,436,820 | 3/1984 | Reiter | . |
| 4,528,187 | 7/1985 | Truglio | 356/246 X |

FOREIGN PATENT DOCUMENTS 0027964  2/1980  Japan .................. 356/413
0029780  3/1980  Japan .................. 356/413

OTHER PUBLICATIONS

Thomas Scientific Catalog, 1986/7, p. 332, order No. 3075-A35; Thomas Scientific, P.O. Box 99, Swedesboro, N.J. 08085-0099.

Primary Examiner—Barry S. Richman
Assistant Examiner—Robert J. Hill, Jr.

[57] ABSTRACT

A device and method for determining characteristics of a fluid sample using optical measurements and changing the optical density range of a sample, e.g., for the second of two required measurements.

14 Claims, 3 Drawing Sheets

DEVICE AND METHOD FOR DETERMINING A CHARACTERISTIC OF A FLUID SAMPLE

BACKGROUND OF THE INVENTION

This invention relates to the quantitative analysis of a component in a biological fluid.

Determination of percent composition of components in a complex biological fluid typically involves techniques for segregating a desired component from the sample, e.g., by column separation, or for altering sample optical density, e.g., by serial dilution or by use of a transparent spacer, and is typically performed by highly skilled laboratory technicians using elaborate laboratory equipment.

One example of the latter procedure is the glycohemoglobin test for blood glucose relied upon by physicians in the treatment of diabetes. Generally, percent glycohemoglobin is determined by comparing the optical density of a diluted blood sample containing a full complement of hemoglobin, with that of a sample containing only hemoglobin in its glycosylated form. Because the total hemoglobin solution is usually at a concentration 5 to 18 times that of the glycohemoglobin solution, the more concentrated solution must be diluted more than the latter to be read with similar accuracy on the same reading device. An application of this method is discussed by Reiter in U.S. Pat. No. 4,436,820.

SUMMARY OF THE INVENTION

According to the invention, a device for use in determining characteristics of a fluid sample by optical measurement by changing the optical density range of a sample comprises a first container defining a volume for receiving a fluid sample, the first container having an open end and being sized and adapted to be disposed between a source of a measuring light beam and a detector in a manner whereby a beam directed from the source to the detector is caused to pass through the first container and the fluid sample contained therein, the container being sized to provide for the beam a path of predetermined effective length through the fluid contained within the first container, a second container defining a volume and having an open end sized and adapted for mating with the first container in leak-tight, open end-to-open end relationship and sized to have an internal diameter substantially the same as that of the first container, the first container and the second container, when assembled in the leak-tight relationship, defining a uniform, continuous volume extending into both containers, and an insert means sized and adapted to be disposed within the volume of the first container in the path of the beam for changing the effective length of the path of the beam through a fluid sample within the first container, the material of the insert means having substantially 100 transmission of light at a selected wavelength, and the insert means comprising a body of predetermined dimension along the path of the beam, and said device including means for positioning the body of the insert means within the volume of the first container, the effective length of the beam passing through a fluid sample within the first container containing the insert means being thereby reduced by the predetermined dimension of the insert means, and, when the first container and the second container are assembled in the end-to-end relationship, the insert means being sized and adapted to slide by gravity between the volumes of the first container and the second container.

In preferred embodiments, the first container has the form of a spectrophotometer cuvette; the first container and the body of the insert means are coaxially aligned; the means for positioning the insert means comprises a plurality of radial protrusions disposed between the insert and the wall of the first container; and the second container includes reagent means for treatment of the fluid sample in a manner to change its chemical composition and thereby its optical density.

According to another aspect of the invention, a method for sequentially determining a characteristic of fluid samples of differing optical densities comprises:

(a) introducing a fluid having a first optical density into a first container sized and adapted to be disposed between a source of a measuring light beam and a detector in a manner whereby a beam directed from the source to the detector is caused to pass through the first container and the fluid sample contained therein;

(b) providing a second container defining a volume and having an open end sized and adapted for mating with the first container in leak-tight, open end-to-open end relationship and sized to have an internal diameter substantially the same as that of the first container;

(c) assembling the first container and the second container in leak-tight, open end-to-open end relationship;

(d) introducing into the volume of the assembled containers an insert means sized and adapted to be disposed within the volume of the first container in the path of the beam for changing the effective length of the path of the beam through a fluid sample within the first container, the insert means further adapted to slide between the first container and the second container in response to gravity;

(e) orienting the assembled containers in a first position to dispose the insert in a first position within the assembled containers and measuring the optical characteristics of the fluid in the container in the path of the beam, between the source and the detector, the beam having a path of predetermined effective length through the fluid within the container;

(f) treating the fluid in the first container to change the optical density of the fluid; and (g) orienting the assembled containers in a second position to dispose the insert in a second position within the assembled containers and measuring the optical characteristics of the fluid in the first container in the path of the beam, between the source and the detector, the beam having a path of relatively different predetermined effective length through the fluid within the first container.

In preferred embodiments of this aspect of the invention, the insert means is disposed within the volume of the first container when the assembled containers are in the first position; the method comprises the further step of treating the fluid with a reagent to result in a sample of different chemical composition and thereby different optical density; and the characteristic determined is percent glycohemoglobin in blood.

According to still another aspect of the invention, a method for sequentially determining a characteristic of fluid samples of differing optical densities comprises:

(a) introducing a fluid having a first optical density into a first container sized and adapted to be disposed between a source of a measuring light beam and a detector in a manner whereby a beam directed from the source to the detector is caused to pass through the first container and the fluid sample contained therein;

(b) disposing the first container of the fluid between a source of a measuring light beam and a detector;

(c) measuring the optical characteristics of the fluid in the container in the path of the beam, between the source and the detector, the beam having a path of predetermined effective length through the fluid within the container;

(d) treating the fluid in the first container to change the optical density and introducing into the container an insert means sized and adapted, when disposed within the volume of the first container in the path of the beam, for changing the effective length of the path of the beam through the fluid, the insert means comprising a body of predetermined dimension along the path of the beam and there being means extending between the insert and the wall of the first container for positioning the body of the insert means within the first container, the effective length of the beam passing through a fluid sample within the first container containing the insert means being thereby reduced by the predetermined dimension of the insert means, the material of the insert means having substantially 100 transmission of light at a selected wavelength;

(e) disposing the first container of the fluid and the insert means in the path of the beam; and (f) measuring the optical characteristics of the fluid in the container in the path of the beam, between the source and the detector, the beam having a path of predetermined reduced effective length, as a result of the insert means within the container.

In preferred embodiments of this aspect of the invention, steps (d), (e) and (f) precede steps (a), (b) and (c), and the insert means is removed from the first container following step (f); the fluid is treated with a reagent to result in a sample of different chemical compositon and thereby different optical density; and the characteristic determined is percent glycohemoglobin in blood.

These and other features of the invention will be understood from the following description of a presently preferred embodiment, and from the claims.

DESCRIPTION OF A PREFEERRED EMBODIMENT

Figure 1:
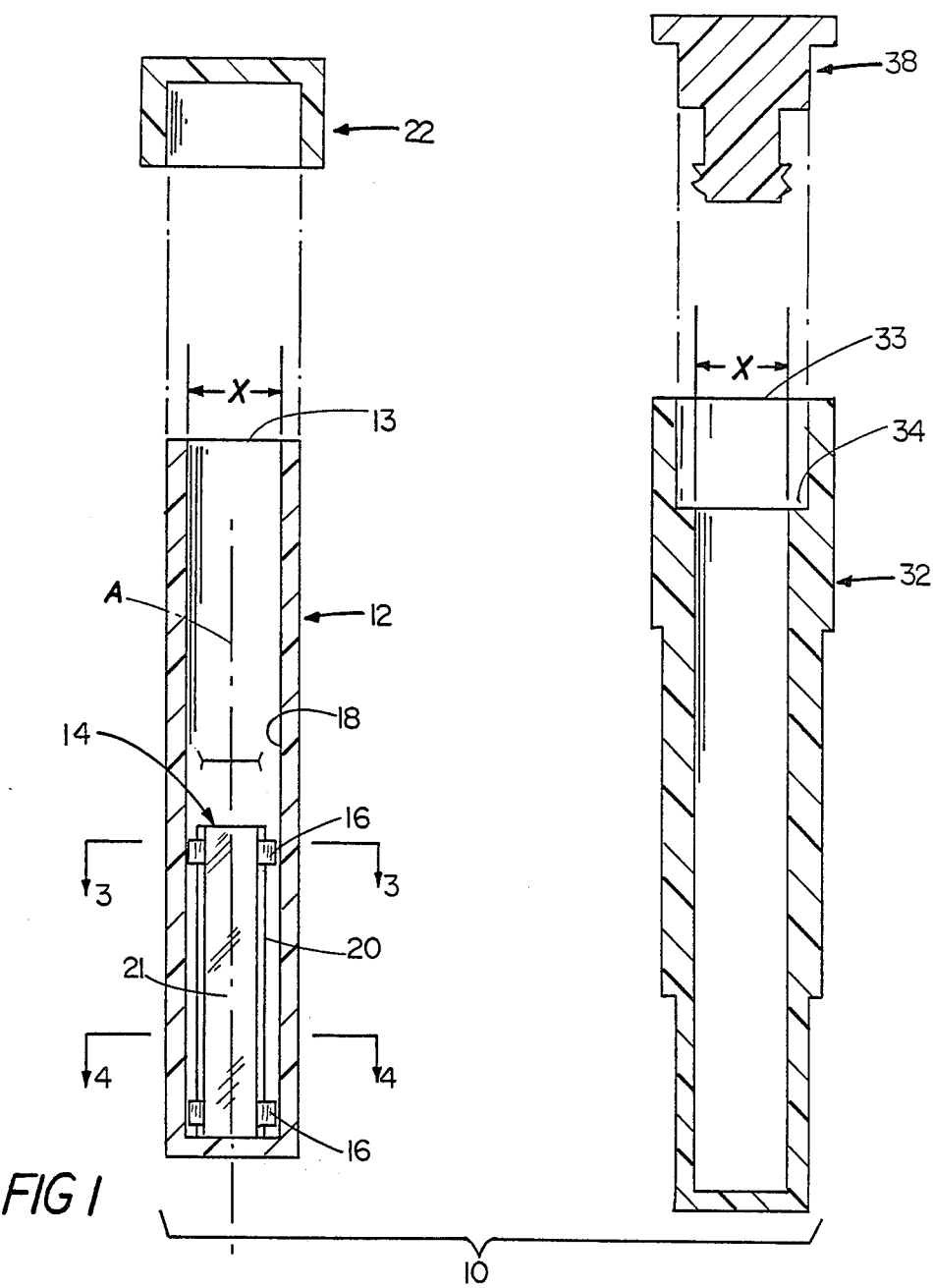
FIG. 1 is a side sectional view of the preferred embodiment of the device of the invention.
Figure 2:
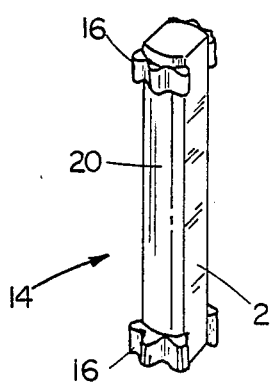
FIG. 2 is a perspective view of a component of the device of FIG. 1.
Figure 3:
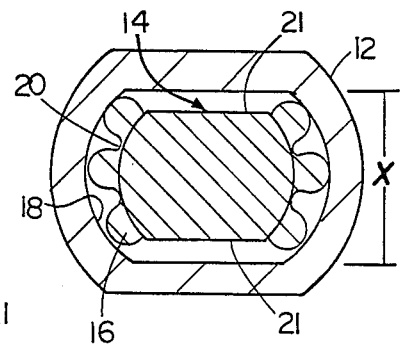
FIGS. 3 and 4 are cross-sectional views taken through 3—3 and 4—4, respectively, of FIG. 1.

Referring to FIGS. 1 through 4, the sample testing device 10 of the invention consists generally of a sample-receiving tube, or first container, 12 with insert 14, and an accessory tube 32 having a shoulder 34 at its open end 33 sized to receive the outer diameter of the open end 13 of tube 12 in leak-tight fit and having an inner diameter, X, sized to match that of tube 12. Both tube 12 and insert 14 are formed of relatively transparent plastic. Tube 12 is equipped with a liquid-tight cap 22 sized to fit snugly over its open end 13 and tube 32 is closed by means of a plug 38.

Figure 4:
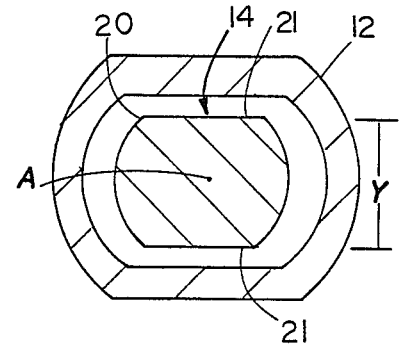
Figure 6A:
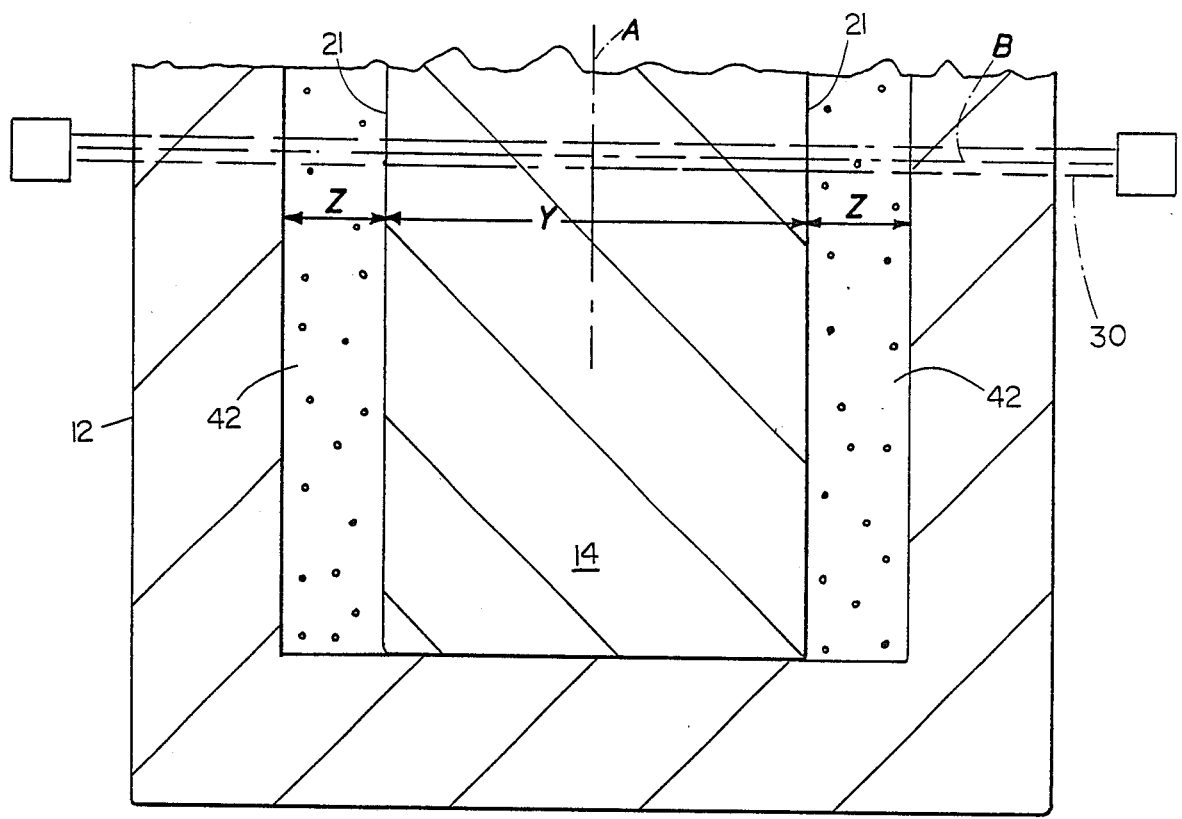
FIGS. 6A and 6B are somewhat diagrammatic enlarged side section views of the device of FIG. 1, depicting sequential optical testing of the sample at different densities.

The tube, or cuvette, 12 is sized for use in conjunction with a spectrophotometer (not shown). The lower portion of the tube is relatively flat on opposed sides, and the inner volume of the tube is shaped to receive the insert only in proper orientation, i.e., as shown in FIGS. 1 and 4, insert 14 is slidingly positioned within the lower portion of tube 12 in a manner to maintain the axis of insert body portion 20 in a position aligned and coaxial with the axis, A, of the tube, with parallel, flat surfaces 21 disposed generally parallel to the flat surfaces of the tube, and perpendicular to the axis, B, of a measuring beam 30, as described below. This is most preferrably achieved by means of ribs extending from the inner wall of the tube 12, above the level of the measuring beam, to lightly engage the body of the insert means for proper alignment and position, or, as shown, by means of radial protrusions 16 which extend from the insert means to lightly engage the inner wall 18 of the tube 12. The diameter, Y, (FIGS. 4 and 6A) of insert body 20, measured between flat surfaces 21, is preselected so that the difference between X and Y (equal to two times Z(FIG. 6A), i.e., the effective optical path length through the fluid sample along axis, B, as discussed more fully below, is a desired percentage of the effective optical path length through tube 12 absent insert 14.

Shoulder 34 of tube 32 is milled to a depth equal to the wall thickness of tube 12, so that when the two tubes 12, 32 are mated mouth-to-mouth, the internal diameter of each is identical and together the tubes form a continuous volume. Thus, when insert 14 is enclosed within the assembled tubes 12, 32 (FIG. 5B), inversion of the assembly causes insert 14 to slide by gravity from tube to tube.

Solutions being spectrophotometrically compared must lie within the same optical density range. The device of the invention enables two (or more) solutions of greatly different optical density to be temporarily and non-chemically manipulated to yield spectrophotometric readings falling within the same optical density range.

Insert 14 is of material having substantially zero optical density, i.e., 100% transmission at a selected wavelength, and tube 12 is relatively light transparent. The diameter Y of insert body 20 is selected to define a solution path length 2Z sufficient to provide a correspondingly reduced overall optical density predetermined to be ideal for the analytes under analysis.

Figure 6B:
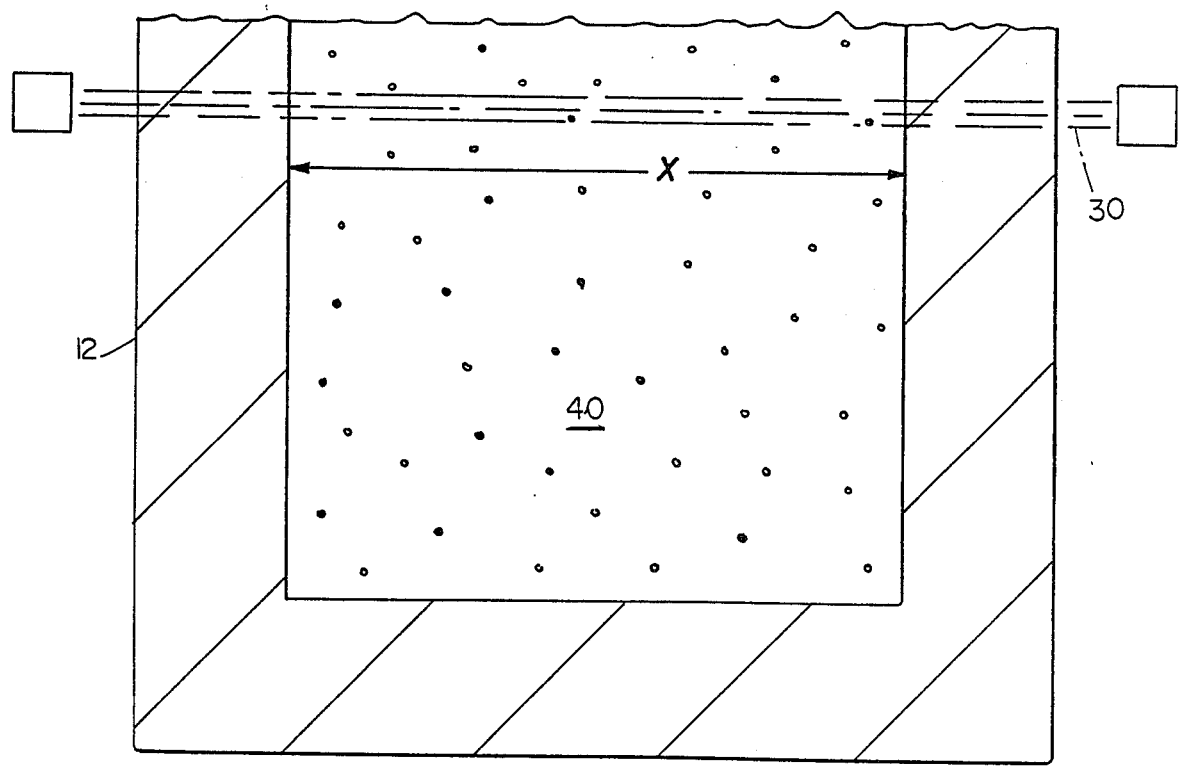

By partially displacing a solution of relatively high optical density with insert 14 through which the analytical beam passes, the total sample density read by the spectrophotometer is reduced by an amount corresponding to the path length of the beam through the insert portion of the beam bath through the tube. Referring to the enlarged view in FIG. 6B, the path length traced by the beam 30 through the less concentrated solution 40 is length, X, the inner diameter of the tube 12. The more concentrated solution (42, FIG. 6A) is analyzed along a beam path which includes the body 20 of insert 14, as depicted in enlarged view FIG. 6A. Therefore, the solution path length through the more concentrated fluid sample has a length 2Z, defined by the distance Z between the inner wall of the tube 12 and the outer wall of insert body 20 at both sides of axis A.

Figure 5A:
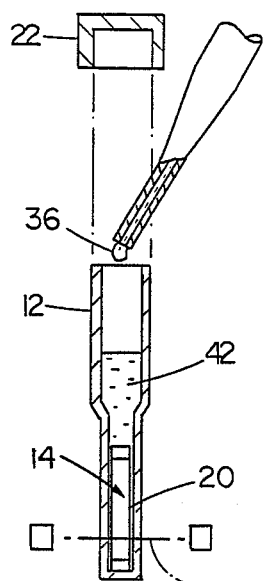
FIGS. 5A through 5E depict procedural steps of the preferred embodiment of the method of the invention.
Figure 5B:
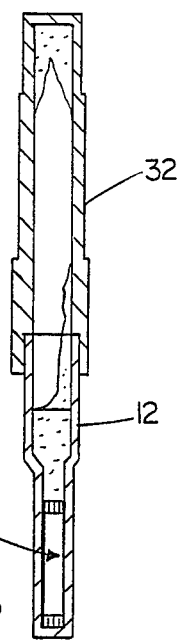
Figure 5C:
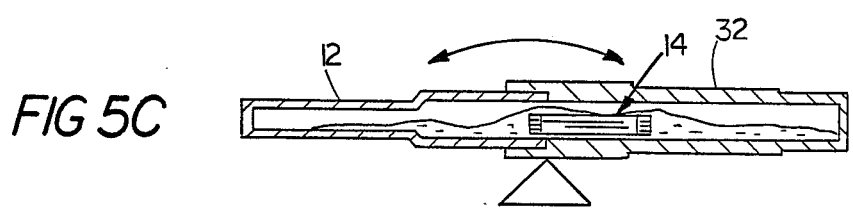
Figure 5D:
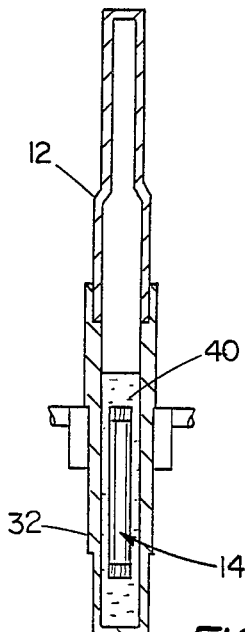
Figure 5E:
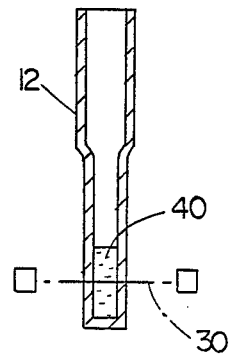
Figure 5E:
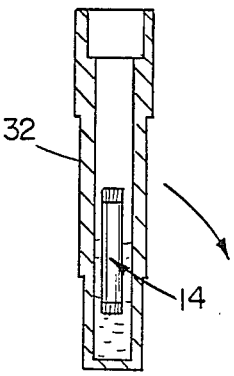

By way of example, one quantitative procedure for which the device of the invention is suited is the determination of percent glycohemoglobin in human blood, as depicted by the non-limiting example shown generally in FIGS. 5 through 5E.

To perform the determination using the device of the invention, one measures approximately ten microliters of the blood 36 to be assayed into first (light transparent) tube 12 containing elution lysing buffer and insert 14. The cap 22 of the tube 12 is replaced and the tube inverted twice so that the elution buffer will lyse the red cells and the resulting lysate will mix uniformly with the buffer. The optical density of the resulting solution in tube, or cuvette, 12 (FIG. 6A) is then read by means of a spectrophotometer (represented by beam 30) which, with 100% transmissive (to selected wavelengths) insert 14 in place, provides a light path 30 through the solution 42 only ⅛ to 1/16 of what it will be when the same tube is subsequently used to measure the optical density of the same solution following removal of desired solution components and insert 14.

After recording the optical density of the relatively concentrated solution containing a full complement of hemoglobin, the cap 22 and plug 38 are removed from the first and second tubes 12, 32, and the tubes are mated mouth-to-mouth by inverting tube 32 over tube 12 (FIG. 5B). Tube 32 contains a reagent, e.g., for this procedure, a cation exchange resin powder, e.g., "Biorex 70", as sold by Biorad Laboratories of Richmond, Calif., which has been pH adjusted to sequester non-glycosylated hemoglobin selectively over glycosylated hemoglobin. The assembly comprising tubes 12, 32, insert 14, and solution 42 is rocked for, e.g., ten minutes, by, e.g., a mechanical rocker, to allow sufficient time for the resin contained in tube 32 to become suspended in solution 42 and sequester non-glycosylated hemoglobin. (The positioning protrusions extending between the inner wall of the tube and the insert are sufficiently spaced from one another to allow fluid to flow around insert 14 between protrusions from one end of mated tubes 12, 32 to the other during inversion of rocking assembly 10.) This fluid motion tends to enhance mixing of the solution and causes insert 14 to pass readily between tubes 12 and 32, further enhancing mixing (FIG. 5C).

Next, the assembly is placed in a centrifuge with the first tube 12 uppermost and spun for, e.g., ten minutes at 500G, pelleting the resin-affiliated non-glycosylated hemoglobin along with insert 14 at the bottom of the accessory tube 32 and leaving glycosylated hemoglobin behind in supernatant 40 (FIG. 5D). Determination of the optical density corresponding to the glycohemoglobin content of the fluid sample is then made by slowly inverting the assembly to decant the supernatant into the sample tube 12. To prevent small amounts of resin from dripping around the insert and down the sides of the tube during the inversion of tube 32 incorporated in the resin is a coarse suspension of an inert material whose density lies between that of the buffer and the resin, e.g. plastic beads of selected density or small pieces of filter paper, e.g., Whatman #17, 1/16 inch squares.

The entire assembly is placed into a spectrophotometer and the optical density of the relatively less concentrated solution 40 is measured and recorded.

Other features and embodiments are within the following claims.

For example, insert 14 can be provided in a variety of shapes, e.g., insert 14 could be a hollow tube, with the reduced path length for the fluid being provided within the insert rather than external to it, or it could be cylindrical.

Also, a resin-confining function may be incorporated within insert 14 to minimize resuspension of the resin pellet. This effect can be achieved by constructing a chamber containing a suitable silicone gel, e.g., "Sure Sep", as sold by General Diagnostics Division of Morris Plains, N.J., in one end of insert 14, the chamber being connected by thin channels to the outside of the insert so that when the tube 12 and insert 14 are inverted and placed in the centrifuge, the chamber portion of insert 14 will be uppermost, and the gel, which is thixotropic, will be expelled during centrifugation and contact that portion of the resin which is not topped by the insert.

Alternatively, as shown in FIG. 5E, following centrifugation, tubes 12, 32 may be uncoupled and the solution transferred from tube 32 by decantation either to its tube mate 12 or to a fresh clear tube 12 (which may be clearer because of not having been handled and not having had a resin in it) and the optical density determined in the unassembled transparent tube 12.

What is claimed is:

1. A device for use in determining a characteristic of a fluid sample by using optical measurements and changing the optical density range of such a fluid sample, comprising:

a first container defining a first volume for receiving a fluid sample, wherein said first container has an inner wall, an internal diameter, and an open end, wherein said first container is sized and adapted to be disposed between a source of a measuring light beam and a detector in a manner such that a beam directed from such a source to such a detector is caused to pass through said first container and a fluid sample contained within the first volume, and wherein said first container is sized to provide for such a beam a path of predetermined effective length through a fluid sample contained within the first volume, a second container defining a second volume, wherein said second container has an internal diameter substantially the same as the internal diameter of said first container and an open end sized and adapted for mating with said first container in a leak-tight, open end-to-open end relationship to define a uniform continuous volume comprising the first volume and the second volume, an insert means comprising a body of predetermined dimeinsion, wherein said insert means is sized and adapted to be disposed within the first volume to change the effective length of the path of a beam directed through a fluid sample in the first volume and to slide by gravity between the first volume and the second volume when said first container and said second container are assembled in open end-to-open end relationship and the insert is disposed within the uniform continuous volume formed thereby, and wherein the material of said insert means has substantially 100% transmission of light at a selected wavelength, and means for positioning the body of said insert means within the first volume such that the effective length of the path of a beam passing through a fluid sample within the first volume is reduced by said predetermined dimension of the body of said insert means.

2. The device of claim 1 wherein said first container has the form of a spectrophotometer cuvette.

3. The device of claim 1 wherein said second container includes reagent means for treatment of a fluid sample in a manner to change its chemical composition and thereby change its optical density.

4. The device of claim 1 wherein said first container, said insert means, and said positioning means are such that when said positioning means positions the body of said insert means in the first volume so that the effective length of the path of a beam passing through a fluid sample within the first volume is reduced by said predetermined dimension of the body of said insert means, the body of the insert means and the first container are coaxially aligned.

5. The device of claim 1 or 4 wherein said positioning means comprises a plurality of radial protrusions, which protrusions are disposed between the body of said insert means and the inner wall of said first container when said positioning means positions the body of said insert means within the first volume so that the effective length of the path of a beam passing through a fluid sample within the first volume is reduced by said predetermined dimension of the body of said insert means.

6. A method for determining a characteristic of a fluid sample, comprising:
   (a) providing a first container defining a first volume, wherein said first container has an open end and an internal diameter, and wherein said first container is sized and adapted to be disposed between a source of a measuring light beam and a dectector in manner such that a beam directed from such a source to such a detector is caused to pass through said first container and a fluid sample contained within the first volume;
   (b) introducing a fluid sample having a first optical density into the first volume;
   (c) providing a second container defining a second volume, wherein said second container has an internal diameter substantially the same as the internal diameter of said first container and an open end sized and adapted for mating with said first container in a leak-tight, open end-to-open end relationship;
   (d) assembling said first container and said second container in such a leak-tight, open end-to-open end relationship to define an assembled volume comprising the first volume and the second volume;
   (e) providing an insert means within the assembled volume, wherein the insert means is sized and adapted to be disposed within the first volume to change the effective length of the path of a beam directed through the fluid sample in the first volume, wherein said insert means is further adapte to slide between the first volume and the second volume in the assembled volume, and wherein said insert means is formed of a material having substantially 100% transmission of light at a selected wavelength;
   (f) orienting the assembled containers in a first position to dispose said insert means in a first position within said assembled volume and measuring an optical characteristic of the fluid sample within the first volume by passing a beam from the source of a measuring light beam to the detector such that the beam passes through said first container and the fluid sample contained within the first volume, said beam having a path of first predetermined effective length through said fluid sample within the first volume when said assembled containers are oriented in the first position;
   (g) treating the fluid sample within the first volume to change the optical density of said fluid sample;
   (h) orienting the assembled containers in a second position to dispose said insert means in a second position within said assembled volume and measuring the optical characteristic of the fluid sample within the first volume by passing the beam from the source of a measuring light beam to the detector such that the beam passes through said first container and the fluid sample contained within the first volume, said beam having a path of second predetermined effective length through said fluid sample within the first volume when said assembled containers are oriented in the second position, said first predetermined effective length being different from said second predetermined effective length; and
   (i) determining the characteristic of said fluid sample from the optical characteristic measurements of steps (f) and (h).

7. The method of claim 6 wherein said insert means is disposed within the first volume when said assembled containers are in said first position.

8. The method of claim 6 wherein the step of treating the fluid sample comprises contacting the fluid sample with a reagent to result in a sample of different chemical composition of thereby different optical density.

9. The method of claim 6, 7, or 8, wherein the fluid sample is blood and the characteristic determined is percent glycohemoglobin.

10. A method for determining a characteristic of a fluid sample comprising:
   (a) providing a first container defining a first volume, wherein said first container has a wall and wherein said first container is size and adapted to be disposed between a source of a measuring light beam and a detector in a manner such that a beam directed from such a source to such a detector is caused to pass through said first container and a fluid sample contained within the first volume;
   (b) introducing a fluid sample having a first optical density into the first volume;
   (c) disposing said first container containing the fluid sample within the first volume between said source of a measuring light beam and said detector;
   (d) measuring an optical characteristic of the fluid sample within the first volume by passing a beam from the source of a measuring light beam to the detector such that the beam passes through said first container and the fluid sample contained within the first volume and has a path of first predetermined effective length through said fluid sample within the first volume;
   (e) treating the fluid sample within the first volume to change the optical density of said fluid sample;
   (f) introducing an insert means within the first volume, wherein the insert means is sized and adapted to be disposed within the first volume to change the effective length of the path of a beam directed through the fluid sample in the first volume, wherein said insert means comprises a body of predetermined dimension and is formed of a material having substantially 100% transmission of light at a selected wavelength, and wherein means extend between the body of the insert means and the wall of the first container to position the body of the insert means within the first volume;

(g) disposing said first container containing the fluid sample and the insert means within the first volume between said source of a measuring light beam and said detector;

(h) measuring the optical characteristic of the fluid sample within the first volume by passing the beam from the source of a measuring light beam to the detector such that the beam passes through said first container and the fluid sample contained within the first volume and has a path of second predetermined effective length through said fluid sample within the first volume, said second predetermined effective length being reduced by the predetermined dimension of the body of the insert means relative to said first predetermined effective length as a result of the insert means being within the first volume during the measuring in step (h); and (i) determining the characteristic of said fluid sample from the optical characteristic measurements of steps (d) and (h).

11. The method of claim 10 wherein the step of treating the fluid sample comprises contacting said fluid sample with a reagent to result in a sample of different chemical composition and thereby different optical density.

12. A method for determining a characteristic of a fluid sample comprising:

(a) providing a first container defining a first volume, wherein said first container has a wall and wherein said first container is sized and adapted to be disposed between a source of a measuring light beam and a detector in a manner such that a beam directed from such a source to such a dectector is caused to pass through said first container and a fluid sample contained within the first volume;

(b) introducing a fluid sample having a first optical density into the first volume;

(c) introducing an insert means within the first volume, wherein the insert means is sized and adapted to be disposed within the first volume to change the effective length of the path of a beam directed through the fluid sample in the first volume, wherein said insert means comprises a body of predetermined dimension and is formed of a material having substantially 100% transmission of light at a selected wavelength, and wherein means extend between the body of the insert means and the wall of the first container to position the body of the insert means within the first volume (d) disposing siad first container containing the fluid sample and the insert means within the first volume between said source of a measuring light beam and said detector;

(e) measuring an optical characteristic of the fluid sample within the first volume by passing a beam from the source of a measuring light beam to the detector such that the beam passes through said first container and the fluid sample contained within the first volume and has a path of first predetermined effective length through said fluid sample within the first volume;

(f) removing the insert means from said first volume;

(g) treating the fluid sample within the first volume to change the optical density of said fluid sample;

(h) disposing said first container containing the fluid sample within the first volume between said source of a measuring light beam and said detector;

(i) measuring the optical characteristic of the fluid sample within the first volume by passing the beam from the source of a measuring light beam to the detector such that the beam passed through said first container and the fluid sample contained within the first volume and has a path of second predetermined effective length through said fluid sample within the first volume, said first predetermined effective length being reduced by the predetermined dimension of the body of the insert means relative to said second predetermined effective length as a result of the insert means being within the first volume during the measuring in step (e); and (j) determining the characteristic of said fluid sample from the optical characteristic measurements of steps (e) and (i).

13. The method of claim 12 wherein the step of treating the fluid sample comprises contacting said fluid sample with a reagent to result in a sample of different chemical composition and thereby different optical density.

14. The method of claim 13, wherein the fluid sample is blood and the characteristic determined is percent glycohemoglobin.

* * * * *

UNITED STATES PATENT AND TRADEMARK OFFICE
CERTIFICATE OF CORRECTION

PATENT NO. : 4,762,798
DATED : August 9, 1988
INVENTOR(S) : Marshall E. Deutsch

It is certified that error appears in the above-identified patent and that said Letters Patent is hereby corrected as shown below:

| | |
|---|---|
| Column 1, Line 57: | "100" should be "100%" |
| Column 3, Line 24: | "100" should be "100%" |
| Column 4, Lines 24-25: | "Z(FIG. 6A)," should be "Z (FIG. 6A)," |
| Column 5, Line 3: | "FIGS. 5" should be "FIGS. 5A" |

<u>In the Claims</u>

| | |
|---|---|
| Column 7, Line 17: | "comprlses" should be "comprises" |
| Column 7, Line 55: | "adapte" should be "adapted" |
| Column 8, Line 39: | "size" should be "sized" |
| Column 10, Line 4: | Insert ";" after "volume" |
| Column 10, Line 5: | "siad" should be "said" |

Signed and Sealed this

Thirtieth Day of May, 1989

Attest:

DONALD J. QUIGG

*Attesting Officer*   *Commissioner of Patents and Trademarks*